US011583387B2

(12) United States Patent
Boysset et al.

(10) Patent No.: US 11,583,387 B2
(45) Date of Patent: Feb. 21, 2023

(54) OPHTHALMIC ASSEMBLY FOR IMPLANTATION IN AN ANTERIOR CHAMBER OF AN EYE OF A PATIENT AND METHOD FOR ACCOMMODATING THE VISION OF THE PATIENT

(71) Applicant: SAV-IOL SA, Neuchatel NE (CH)

(72) Inventors: Max Boysset, Bonvillars (CH); Alexandre Pascarella, Colombier (CH); Julien Jacot, Marin-Epagnier (CH)

(73) Assignee: SAV-IOL SA, Neuchatel NE (CH)

( * ) Notice: Subject to any disclaimer, the term of this patent is extended or adjusted under 35 U.S.C. 154(b) by 151 days.

(21) Appl. No.: 16/962,029

(22) PCT Filed: Jan. 15, 2019

(86) PCT No.: PCT/EP2019/050986
§ 371 (c)(1),
(2) Date: Jul. 14, 2020

(87) PCT Pub. No.: WO2019/141695
PCT Pub. Date: Jul. 25, 2019

(65) Prior Publication Data
US 2020/0397563 A1  Dec. 24, 2020

(30) Foreign Application Priority Data
Jan. 16, 2018  (EP) .................................. 18151949

(51) Int. Cl.
*A61F 2/16* (2006.01)
*A61F 2/48* (2006.01)

(52) U.S. Cl.
CPC .......... *A61F 2/1605* (2015.04); *A61F 2/1627* (2013.01); *A61F 2/1635* (2013.01);
(Continued)

(58) Field of Classification Search
CPC ...... A61F 2/1627; A61F 2/1635; A61F 2/482; A61F 2250/0003; A61F 2250/0002; A61F 2002/1689
See application file for complete search history.

(56) References Cited

U.S. PATENT DOCUMENTS

| 2006/0155372 | A1 | 7/2006 | Coroneo | |
| 2007/0260307 | A1* | 11/2007 | Azar | ..................... A61F 2/1627 623/6.37 |

(Continued)

FOREIGN PATENT DOCUMENTS

| AU | 2006200142 A1 | 7/2006 | |
| DE | 102007048859 A1 * | 4/2009 | ........... A61F 2/1601 |

(Continued)

OTHER PUBLICATIONS

Written Opinion issued in Application No. PCT/EP2019/050986 dated Jun. 26, 2019.
(Continued)

*Primary Examiner* — Javier G Blanco
(74) *Attorney, Agent, or Firm* — DLA Piper LLP (US)

(57) ABSTRACT

An ophthalmic assembly for implantation in an anterior chamber of an eye of a patient to provide accommodation of the vision to said patient comprises a variable-focus lens and an actuator for modifying the focal length of the variable-focus lens. The ophthalmic assembly comprises an autofocus system configured to determine a distance parameter of an object that the patient's eye is looking at; a signal processing unit arranged to convert said distance parameter into a focal length value of the variable-focus lens; and an actuator control unit configured to control the actuator as a function of the focal length value received from said signal processing unit. A method for accommodating the vision of a patient using an opthamalic assembly is also disclosed.

4 Claims, 2 Drawing Sheets

(52) U.S. Cl.
CPC ....... *A61F 2/482* (2021.08); *A61F 2002/1689* (2013.01); *A61F 2250/0002* (2013.01); *A61F 2250/0003* (2013.01)

(56) References Cited

U.S. PATENT DOCUMENTS

| | | | | |
|---|---|---|---|---|
| 2008/0208335 | A1* | 8/2008 | Blum | G02C 7/04 623/6.22 |
| 2009/0032679 | A1* | 2/2009 | Holladay | A61B 3/112 250/201.2 |
| 2012/0236257 | A1 | 9/2012 | Hillis et al. | |
| 2012/0290084 | A1* | 11/2012 | Coroneo | A61F 2/1635 623/6.13 |
| 2014/0327875 | A1* | 11/2014 | Blum | G02C 7/083 623/6.22 |
| 2015/0378177 | A1 | 12/2015 | Blum et al. | |
| 2016/0085089 | A1* | 3/2016 | Hillis | G02C 7/101 351/205 |
| 2017/0075140 | A1 | 3/2017 | Hillis et al. | |
| 2017/0189169 | A1 | 7/2017 | Haddock et al. | |
| 2018/0217402 | A1* | 8/2018 | Larmagnac | G02B 3/14 |
| 2019/0086693 | A1 | 3/2019 | Blum et al. | |

FOREIGN PATENT DOCUMENTS

| | | |
|---|---|---|
| EP | 2 461 572 A1 | 6/2012 |
| WO | WO 2007/131014 | 11/2007 |

OTHER PUBLICATIONS

International Search Report issued in Application No. PCT/EP2019/050986 dated Jun. 26, 2019.

* cited by examiner

OPHTHALMIC ASSEMBLY FOR IMPLANTATION IN AN ANTERIOR CHAMBER OF AN EYE OF A PATIENT AND METHOD FOR ACCOMMODATING THE VISION OF THE PATIENT

CROSS REFERENCE TO RELATED APPLICATIONS

This application is a U. S. National Stage Application of International Application No. PCT/EP2019/050986 filed Jan. 15, 2019, which claims priority from European Patent Application No. 18151949.7 filed Jan. 16, 2018. The entirety of all the above-listed applications are incorporated herein by reference.

TECHNICAL FIELD

The present invention concerns an ophthalmic assembly for implantation in an anterior chamber of an eye of a patient to provide accommodation of the vision to said patient. The ophthalmic assembly comprising a variable-focus lens and an actuator for modifying the focal length of the variable-focus lens.

The invention further concerns a method for accommodating the vision of a patient by means of an ophthalmic assembly implanted in an anterior chamber of an eye of said patient, said ophthalmic assembly comprising a variable-focus lens, an actuator, an autofocus system, a signal processing unit, an actuator control unit and a power supply.

BACKGROUND ART

Currently, a large number of people undergo operations for cataracts. During this operation, the crystalline, opacified through disease, is removed and replaced by an artificial lens.

A side effect inherent to any cataract surgery is the loss of accommodation of the patient's eye. The crystalline is replaced, generally by a posterior chamber intraocular lens, which leads consequently to remove at the same time the accommodation function, essential for good vision at varying distances. This has the consequence that the cataract operated patient has to wear glasses to have a good vision at any distance.

In phakic eyes, i.e. in eyes in which the natural lens is not removed, problems due to loss of accommodation appears also with age-related presbyopia, which is a decrease of the accommodation capacity of the natural lens. The patient is therefore also dependent on glasses and possibly progressive glasses.

Several intraocular lenses have been developed to re-create accommodation or pseudo-accommodation and to get rid of eyeglasses dependence. Such lenses are for example multifocal lenses, lenses with extended depth-of-focus or accommodative lenses. Each of these optical or mechanical methods have their own interest and characteristics, but they can suffer from some drawbacks. In particular, any methods based on optical elements on the lens surfaces will use at the end a finite amount of light intensity. This light intensity is distributed for each vision distance with more or less loss of energy, and more or less adverse effects such as halos, glares or ghost images.

Accommodative lenses have been developed to overcome the above-mentioned drawbacks. Currently, most of these accommodative lenses are based on a mechanical motion. These accommodative lenses to be placed in the capsular bag of a patient's eye are designed to be driven by the ciliary muscle to move a multi-lens optical system or to change the radius of curvature of optical elements. The key issue with this method is that the ciliary muscle loses its capability with age due to the previous conditions (cataract, presbyopia, etc.). This ciliary muscle contraction reduction and effects related to capsular fibrosis often does not allow providing enough motion to compensate the expected level of accommodation.

Some other accommodative lenses are not based on mechanical motion but on a displacement of liquids. Such lenses are formed of a cylindrical fluid chamber containing two non-miscible fluids in contact with each other over a meniscus and having different indices of refraction. One of the fluids is in contact with two electrodes. The variation of a voltage between both electrodes modifies the shape of the meniscus and thus, the focal length of this lens.

This lens has several drawbacks. In particular, it is used to treat a vision disorder in a patient. This means that, depending on the extent of the disorder, the width of the lens must be quite important to cover a great range of disorders. In cases where the extent of the disorder is important, it can happen that the disorder cannot be corrected by such a lens.

Due to the shape and size of the lens, it has to be placed in the posterior chamber of the patient's eye. This means that the lens periphery receives little light, depending on the size of the iris. This is a severe drawback if the lens periphery is used to host peripheral devices. Moreover, this technology requires a great amount of energy, which is not compatible with the constraints linked to the small available size.

DISCLOSURE OF INVENTION

The present invention proposes to overcome the drawbacks of ophthalmic assemblies of the prior art in providing an assembly that allows accommodation of the view of the patient, without the need to wear glasses. In addition, the accommodation can be performed for people whose ciliary muscles have lost their contraction capacity, particularly because of the age of the person or because of a disease. This ophthalmic assembly is compatible with existing intraocular lenses implanted for correcting the vision of the patient.

According to a first aspect, provision is made for an ophthalmic assembly for implantation into an anterior chamber of an eye of a user, the ophthalmic assembly comprising a support upon which is disposed:
  a variable-focus lens having a variable dioptric power;
  an autofocus system configured to receive light from a target object upon which the user's gaze falls and to determine a distance parameter for the target object;
  a processor configured to convert the distance parameter to a control value;
  an actuator configured to cause the dioptric power of the variable-focus lens to vary according to the control value; and
  at least one power source to provide power to the components of the assembly;
  characterised in that:
  the autofocus system comprises:
    an autofocus lens system located on the support adjacent to the variable-focus lens; and
    at least one autofocus sensor configured to measure a contrast value of at least part of an image formed on at least a part of the autofocus sensor by light passing through the autofocus lens system;
  the autofocus lens system being configured to cause light passing through at least a part of the autofocus lens system from the target object upon which the user's gaze falls to form an image which causes a maximal contrast to be measured on a part of the autofocus sensor, the autofocus system being configured to use a parameter of the autofocus lens system when the maximal contrast is measured to determine the distance parameter and to communicate the distance parameter to the processor.

According to a second aspect, provision is also made for an ophthalmic assembly set for implantation into two anterior chambers of two eyes of a user, the ophthalmic assembly set comprising two ophthalmic assemblies according to any of the preceding claims, one assembly for each eye, each of the assemblies further comprising means for communicating with the other assembly.

According to a third aspect, a method is disclosed for accommodating a vision of a user by means of an ophthalmic assembly implanted into an anterior chamber of an eye of the user, the ophthalmic assembly comprising a support upon which is disposed:
  a variable-focus lens having a variable dioptric power;
  an autofocus system configured to receive light from a target object upon which the user's gaze falls and to determine a distance parameter for the target object;
  a processor configured to convert the distance parameter to a control value;
  an actuator configured to cause the dioptric power of the variable-focus lens to vary according to the control value; and
  at least one power source to provide power to the components of the assembly;
  wherein the autofocus system comprises:
  an autofocus lens system located on the support adjacent to the variable-focus lens; and
  at least one autofocus sensor configured to measure a contrast value of at least part of an image formed on at least a part of the autofocus sensor by light passing through the autofocus lens system;
  the method comprising:
  determining a distance parameter for the target object using the autofocus system;
  converting the distance parameter to a control value using the processor; and
  adjusting the dioptric power of the variable-focus lens using the actuator, said adjustment being based on the control value.

According to this invention, a patient into which an ophthalmic assembly has been implanted may have an accommodation similar to the accommodation of a normal, healthy eye. This ophthalmic assembly can be applied to a patient who has lost the accommodation function, for example because of a cataract. This ophthalmic assembly can also be implanted in the eye of a patient who has lost the accommodation function, for example because of age, while maintaining his crystalline lens. In both cases, the ophthalmic assembly is able to restore the accommodation function to the user's eyes.

During an operation of implantation of an intraocular lens, the optical and geometrical characteristics of the lens implanted to replace of the crystalline are calculated based in particular on the correction to be made to the patient's vision and on the geometrical characteristics of the patient's eye. The lens is then sized and positioned according to these parameters. Because of the difficulty of taking very precise measurements of the characteristics of the eye, because the lens can move slightly in the eye and because the characteristics of the patient's eye can change over time, the implanted lens is not always perfectly adapted to the patient. The ophthalmic assembly according to the invention makes it possible to correct the difference between an optimal theoretical lens and the lens actually implanted in the patient's eye to reach emmetropia. Moreover, as the ophthalmic assembly restores the accommodation function to the patient, the patient can do without glasses, regardless of the distance of vision.

BRIEF DESCRIPTION OF DRAWINGS

The present invention and its advantages will be better understood with reference to the enclosed drawings and to the detailed description of a specific embodiment, in which.

MODE FOR CARRYING OUT THE INVENTION

Figure 1:
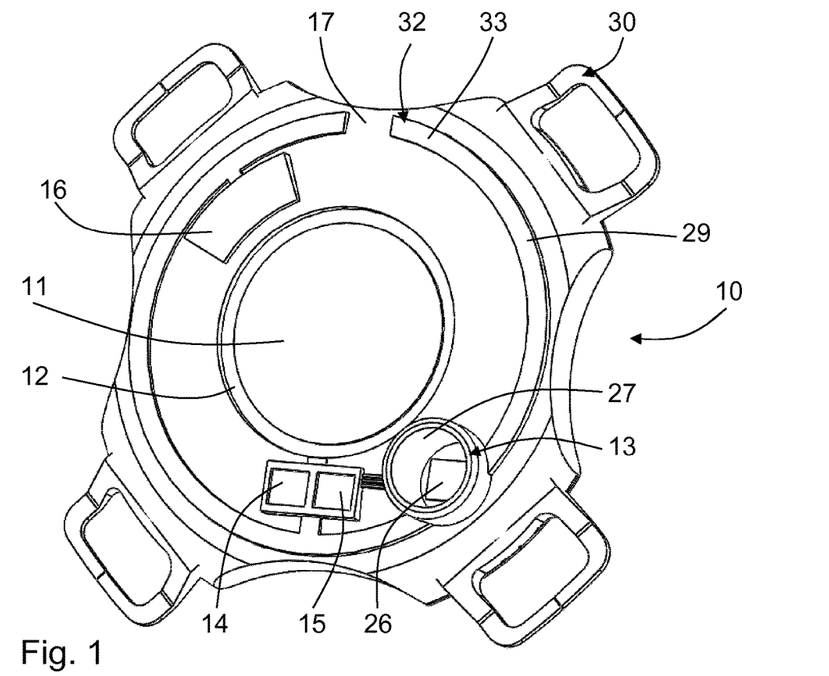
FIG. 1 illustrates an ophthalmic assembly according to the present invention.
Figure 2:
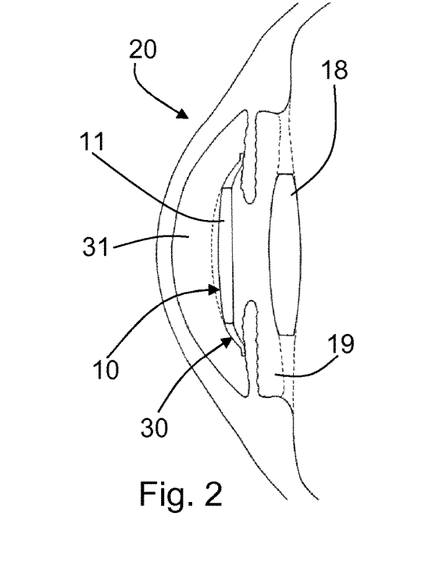
FIG. 2 shows an ophthalmic assembly implanted in an eye of a patient.

With reference to the drawings and in particular to FIG. 1, the ophthalmic assembly 10 according to the invention comprises a variable-focus lens 11, an actuator 12, an autofocus system 13, a signal processing unit 14, an actuator control unit 15, a power supply 16 and a support 17. In some embodiments, the processing unit and the actuator control unit may comprise a single module. The term processor 14, 15 may therefore be used to describe a combination of the processing unit and the actuator control unit.

The variable-focus lens 11 is in principle intended to support accommodation of the vision of the patient and not to correct the vision of the patient. The correction of vision may be unnecessary in the case for example where the vision of the patient is satisfactory and only the accommodation's function is deficient. The correction could also be supported by a conventional intraocular lens 18, such an intraocular lens then being generally implanted in a posterior chamber 19 of the patient's eye 20. The correction could also be supported by contact lenses or spectacles.

The variable-focus lens 11 as used in the ophthalmic assembly 10 according to the invention can take different forms. In general terms, the variable-focus lens can be said to have a variable dioptric power. Different embodiments of variable-focus lens have different features to bring about the variation in the dioptric power of the lens. According to the different embodiments, the actuator may take one of several different forms. The actuator is configured to cause the dioptric power of the variable-focus lens to vary according to a control value received from the processor. The processor is arranged to generate the control value based on a distance parameter received from the autofocus system, which will be described later.

Figure 3:
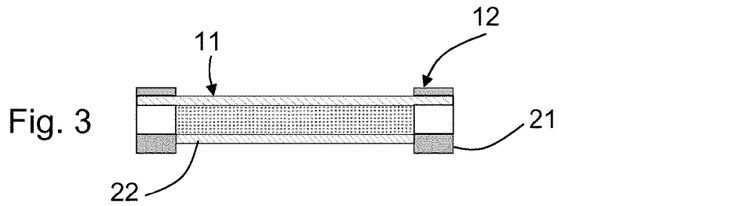
FIG. 3 is a schematic view of a first embodiment of a lens used in an ophthalmic assembly according to the invention, in a first configuration.
Figure 4:
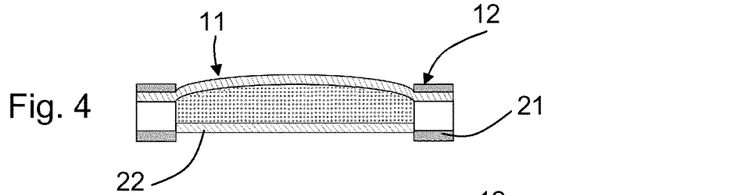
FIG. 4 shows the lens of FIG. 3, in a second configuration.
Figure 5:
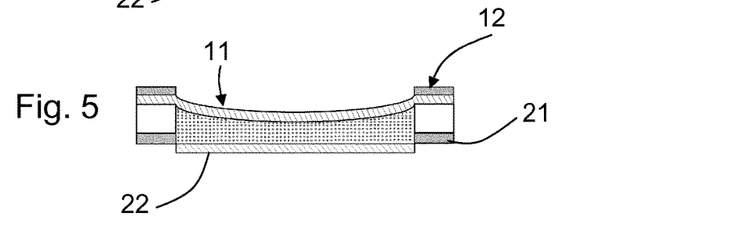
FIG. 5 shows the lens of FIGS. 3 and 4 in a third configuration.

According to a first embodiment illustrated by FIG. 3-5, the variable-focus lens 11 is made of a deformable material and/or has a deformable shape and usually contains a fluid, such as liquid. Such a lens is called "deformable lens". Typically, such a variable-focus lens can comprise a membrane made of an elastic transparent material such as for example silicone, flexible acrylic materials or any adequate elastomeric non-permeable membrane. The actuator 12 of the ophthalmic assembly 10 comprises at least one compression element 21 disposed on the periphery of the lens on the support 17. In some embodiments, the actuator comprises two compression elements 21 disposed on either side of the lens, these two compression elements being movable relative to each other. When one of the compression elements 21 is displaced with respect to the other or with respect to the lens, at least one of said compression elements acts on the deformable lens and modifies its shape. This change of shape is illustrated by FIGS. 3 to 5. In FIG. 3, the lens 11 has two parallel faces. Parallel light beams entering into the patient's eye remain parallel when they exit the lens. In FIG. 4, the lens 11 has a convex surface shape. The lens illustrated by FIG. 5 has a concave surface shape. The membrane of the variable-focus lens of this embodiment can be said to be an element which has a deformable shape because its shape may be altered when acted upon by the compression element.

This change in shape of the lens has the effect of changing the focal length of the lens. Controlling the displacement of the compression elements 21 thus makes it possible to control the focal length of the variable-focus lens 11.

According to an advantageous embodiment, the variable-focus lens 11 comprises a rigid transparent stationary face 22. The compression element 21 moves relative to this rigid face 22 of the lens and thus induces a deformation of this variable-focus lens 11.

According to another embodiment, one of the compression elements comprises a transparent piston in contact with one of the faces of the lens 11. This piston is capable of acting on one face of the variable-focus lens so as to deform it. According to an embodiment, the transparent piston is integral with one of the compression members.

In the various embodiments of the actuator 12 mentioned above in which the actuator comprises two compression elements 21, the displacement of these compression elements is a relative displacement, i.e. one of the elements moves relative to the other. More specifically, the distance between both elements can increase or decrease. This means that one of the compression elements can remain stationary while the other is moved or the two elements can approach or move away from each other while being both mobile.

According to another variant, the actuator 12 comprises at least one electrode, for example an annular electrode, disposed on the support 17, on the periphery of the lens. This lens comprises a membrane made of an electroactive polymer. By applying a voltage to the electrode, the membrane is deformed, which has the effect of changing the focal length of the lens. The membrane is an element having a deformable shape.

Other types of lenses with variable focal length can also be used, in particular non-deformable lenses.

Among such non-deformable variable-focus lenses, mention may be made of variable-focus lenses containing two immiscible liquids. One of these liquids is electrically conductive, the other liquid being electrically insulating. These liquids also have a different refractive index and are separated by an interface. The interface between the two immiscible liquids forms a meniscus whose shape acts on the optical path of the incident light. The shape of this meniscus can be modified in a controlled manner by applying a potential difference between the two liquids. A change in the shape of the meniscus has the effect of changing the focal length of the variable-focus lens. In this embodiment, the meniscus can be said to be an element of the variable-focus lens, which meniscus has a deformable shape.

Generally, such lenses having a meniscus of deformable shape are formed within a rigid container. However, it is possible to combine such a lens with the previous embodiments, namely with a deformable lens so that the shape of at least a part of the container is also deformable. For example, a flexible membrane on one side of the lens through which light from the object passes. Alternatively, both faces of the lens may have flexible membranes.

According to another variant, a variable-focus lens may comprise a zone containing liquid crystals. These liquid crystals have a refractive index which varies according to the electric field applied to them. The control of the electric field applied to the liquid crystals makes it possible to adjust the refractive index and consequently to adjust the focal length of the variable-focus lens.

Figure 6:
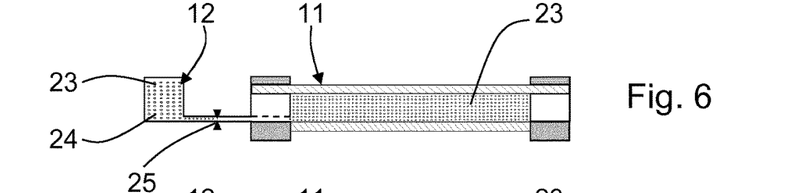
FIG. 6 is a schematic view of a second embodiment of a lens used in an ophthalmic assembly according to the invention, in a first configuration.
Figure 7:
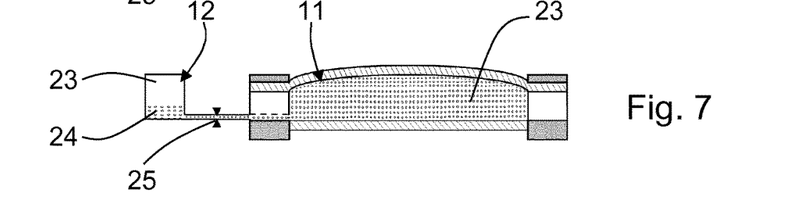
FIG. 7 shows the lens of FIG. 6, in a second configuration.

According to yet another variant, illustrated by FIGS. 6 and 7, the lens 11 is a deformable lens and contains at least one liquid 23, the inside of the lens being connected to a reservoir 24 and a pump 25 acting as an actuator 12. The pump 25 makes it possible to modify the quantity of liquid 23 contained in the lens and thus to deform this lens 11. This has the effect of changing the focal length of the variable-focus lens. Again, in this embodiment, a flexible membrane of the lens can be said to be the element having a deformable shape.

The actuator 12 is dependent on the type of variable-focus lens and of parameters such as the shape of the lens, the material in which it is made, its content, etc.

According to the embodiment illustrated in FIG. 3-5, the actuator 12 comprises two annular compression elements 21 disposed on either side of the periphery of the lens, on the support 17. These compression elements are of capacitive, electrostatic or piezoelectric type, for example. The compression elements are separated by a predefined distance in the absence of electrical excitation. According to an advantageous embodiment, this predefined distance can be set individually. This predefined distance corresponds to a focal length of the variable-focus lens, called default focal length.

In the case of a variable-focus lens containing two immiscible liquids, the actuator 12 is formed of an electrical source capable of generating a potential difference in a controlled manner.

In the case where the modification of the shape of the variable-focus lens is performed by modifying a quantity of liquid contained in a deformable envelope, the actuator 12 comprises the pump 25 and the liquid reservoir 24.

It is clear that the actuator 12 and its mode of operation depend on the type of variable-focus lens used and how that focal length is modified and controlled.

The autofocus system 13 of the ophthalmic assembly 10 according to the invention has the function of determining what should be the focal length of the variable-focus lens 11 to allow optimal vision by the user. It is clear that this focal length varies according to the distance of the object that the user is looking at. In order to achieve this goal, the autofocus system determines a distance parameter, the nature of which varies according to the implementation.

The autofocus system 13 is advantageously disposed on the support 17, near the variable-focus lens 11, in an area of the ophthalmic assembly that receives enough light from the object at which the user is looking. For example, FIG. 1 and FIG. 8 both show the autofocus systems being located adjacent to their respective variable-focus lens.

In a first embodiment, the autofocus system 13 comprises an autofocus sensor 26 and an autofocus lens system 27. In this embodiment, the autofocus lens system comprises a single autofocus lens 27, wherein the distance between the autofocus sensor and the autofocus lens is changeable. When the user is looking at an object, the position of the autofocus lens, or more precisely the distance between the autofocus lens 27 and the autofocus sensor 26 is modified. An image of the object is formed on the autofocus sensor 26 and the contrast of this image is measured. The autofocus lens 27 is moved until the measured contrast is maximal. The distance between the autofocus lens 27 and the autofocus sensor 26 is then determined, this distance forming the distance parameter of the autofocus system.

By placing the autofocus system near the variable-focus lens, this ensures that the autofocus lens system is placed close to the variable-focus lens so that the autofocus system works on an image which is substantially the same as the image formed in the user's eye from the target object upon which the user's gaze falls. In the embodiment described above, the autofocus lens may be described as a micro-lens in that it has a diameter of less than 1 millimetre (1 mm) and may be as small as 10 micrometres (10 um) in diameter. This allows for the distance between the autofocus lens and the variable-focus lens to be minimised.

According to an embodiment, the position of the autofocus system may be chosen to be anywhere around the periphery of the variable-focus lens, thus allowing for different positions to be selected according to any particular constraints which need to be considered during placement of the assembly in an eye. For example, it may be desirable for the orientation of the assembly, once placed in the eye, to have a particular orientation. Examples of particular orientations include inferior, nasal or temporal orientations, and the choice of orientation may be made based on visual field orientations and/or eyelid requirements. According to other embodiments, a plurality of autofocus systems may be provided on one assembly so that one or other of the autofocus lens systems may be selected depending on the favourability of its orientation.

Figure 8:
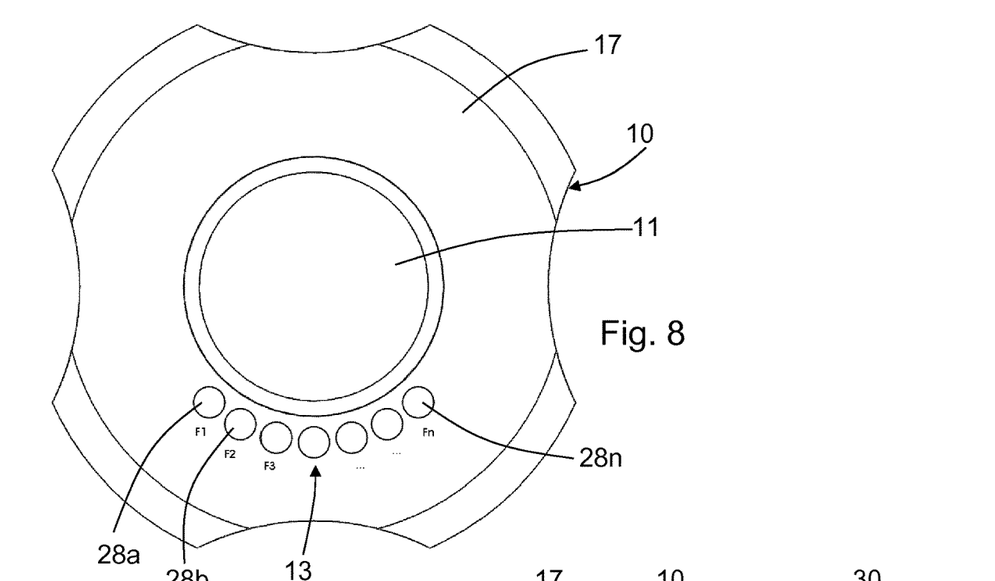
FIG. 8 illustrates a part of a specific embodiment of an ophthalmic assembly according to the invention.

In another embodiment, illustrated by FIG. 8, the autofocus system 13 comprises an autofocus lens system having a plurality of lenses 28a, 28b, . . . , 28n each having different fixed focal lengths from each other and being disposed adjacent to each other. Each lens generates an image on at least a part of an autofocus sensor. Since the autofocus lens system is located close to the variable-focus sensor, the plurality of images formed by the plurality of autofocus lenses are substantially the same image of the target object upon which the user's gaze falls. A separate autofocus sensor can be used for each of the separate lenses or on the contrary, a single autofocus sensor can be used for all the lenses, a different area or region of the autofocus sensor being dedicated to each lens.

According to various embodiments, the plurality of autofocus lenses of the autofocus lens system may be described as being micro-lenses in that they may have a diameter of less than 1 millimetre (1 mm) and may even be as small as 10 micrometres (10 um) in diameter. This allows for the distance between the autofocus lens and the variable-focus lens to be minimised.

The plurality of micro-lenses may be said to form a micro-lens array. Embodiments of the present invention may therefore comprise an autofocus system having an autofocus lens system comprising a micro-lens array and one or more autofocus sensors behind the micro-lens array to receive light from the target object which passes through the micro-lens array. The autofocus lens system can be said to form part of a range finder.

FIG. 8 can therefore be said to illustrate an embodiment of the ophthalmic assembly having an autofocus system comprising an autofocus lens system having a micro-lens array. This can be said to function as a range finder. The micro-lenses each have different fixed focal lengths and each micro-lens within the array generates a corresponding image of a target object upon which the user's gaze is directed on an autofocus sensor. A separate autofocus sensor may be used for each of the separate micro-lenses of the autofocus lens system. Otherwise, a single autofocus sensor may be used for all the micro-lenses, a plurality of different regions or areas of the autofocus sensor each corresponding to one from the plurality of micro-lenses. The contrast may be measured for each of the images formed by the autofocus micro-lens array. The focal length of the micro-lens producing the image with the highest contrast may be used to provide the distance parameter for the autofocus system. FIG. 8 shows an example of how micro-lens array may be arranged on the support of the ophthalmic assembly, adjacent, and preferably close, to the variable-focus lens. Other arrangements are possible as long as the close proximity of the micro-lens array to the variable-focus lens and of each of the micro-lenses in the array to each other is respected. The number of micro-lenses in the array may also be selected according to design needs.

Two main types of micro-lens exist and are known as gradient index micro-lenses (GRIN) and micro-Fresnel lenses. These are further discussed later in the present disclosure. GRIN micro-lenses may be coated with various different coatings to provide a desired refractive index. Consequently, each of the lenses of a particular micro-lens array may be coated differently. For example, a first lens in the array may have a coating of a first material, a second lens in the array may have a coating of a different material and a third lens in the array may have a coating including layers of both the first and second materials. Partial polymerisation techniques may also be used, e.g. using UV light, to create a gradient of different refractive indices across an array of micro-lenses. Otherwise, the process for making a micro-Fresnel lens may be employed to make a complete array of micro-lenses each having different refractive indices.

It is also possible to print an array of micro-lenses. For example, a drop-on-demand technique (DoD) may be used, similar to inkjet printing, where a substrate is passed beneath a heated print head having a nozzle for expelling drops of fluid at ambient pressure onto the substrate as it passes. The print head has a piezo transducer, which may be controlled by providing suitably formatted data to a print head driver for providing the required drops of fluid onto the substrate. For a fluid comprising a suitable polymer, and where the substrate is a part of the autofocus sensor of the ophthalmic assembly described herein, a series of plano-convex polymer drops forming the micro-lenses may thus be deposited on top of the autofocus sensor. By choosing different polymers and by changing printing parameters, such as the data used for the print head driver or the temperature of the print head or the size and/or shape of the nozzle of the print head, lenses having different fixed focal lengths can be made.

A micro-lens array may also be manufactured wherein each of the micro-lenses is an optofluidic lens. Such lenses may be of the fixed-focus type or the variable-focus type. It has already been mentioned that autofocus lens systems for use in embodiments of the present invention may comprise a deformable lens.

These manufacturing techniques allow for suitable micro-lens arrays to be produced for the ophthalmic assemblies described herein, having autofocus systems having micro-lens arrays in which suitably small lenses may be placed very close together and close to the variable-focus lens, with the refractive indices of each micro-lens of the array being suitably controllable to provide the different refractive indices.

The contrast is measured for each of the images formed by the autofocus lenses 28. The focal length of the lens producing the image with the highest contrast forms the distance parameter of the autofocus system 13.

Alternatively, it is possible to extrapolate the focal length that would produce the maximum contrast from the measurement of the contrast of at least two adjacent images and preferably at least three images.

Embodiments of the present invention whose autofocus lens systems include a micro-lens array provide advantages related to a reduction in energy consumption and therefore prolongation of battery life because of fewer moving parts to which energy requires to be supplied.

According to another embodiment, the autofocus system 13 comprises at least one variable-focus autofocus lens. The focal length of this lens is modified and the contrast on the image obtained is determined. The focal length producing the image with the highest contrast forms the distance parameter of the autofocus system.

According to some embodiments, variable-focus lenses used within the autofocus system may be of the deformable type such as those which were described above for the variable-focus lens responsive to the distance parameter provided by the autofocus system.

The value of the distance parameter of the autofocus system 13 is transmitted to the signal processing unit 14. This signal processing unit 14 comprises a calculation module in charge of converting the value of the distance parameter of the autofocus system into a value of the focal length of the variable-focus lens 11. The calculation module can be calibrated globally or on the contrary, individually for each user.

The value of the focal length determined by the calculation module of the signal processing unit 14 is then transmitted as a target value to the actuator control unit 15. This actuator control unit 15 then acts on the actuator 12 so that the variable-focus lens 11 adjusts its focal length according to the target value given to it.

It is clear that the focus adjustment is done in a manner that depends on the type of variable-focus lens 11 and the type of actuator 12. Thus, if the variable-focus lens 11 is deformable by means of capacitive, electrostatic or piezo-electric compression elements 21, the control unit 15 of the actuator will act on the voltage applied to the compression elements. If the variable-focus lens 11 has a shape that can be modified by injection or suction of a liquid, the control unit will act on the pump 25 for changing the amount of liquid 23 contained in the lens with variable focus.

The autofocus system 13 as well as the signal processing unit 14 and the actuator control unit 15 require at least one source of energy or power supply 16. This power supply can take different forms. It is also possible to provide not only one, but several different sources of energy. A first source of energy may be a battery, for example disposed at the periphery of the support 17. A second energy source may be a supercapacitor or a rechargeable battery. It is also possible to equip the support 17 with a photovoltaic cell which can be transparent or not. The user's body can also be used as a source of energy. This energy source can for example recover energy from body heat, muscle movements, fluid flow, etc.

It should be noted that even if the energy originates, for example, from movements of muscles, this cannot be compared with the systems of the prior art in which the deformation of the accommodative lens is generated by the ciliary muscle. Indeed, in the prior art, the deformation of the lens is directly related to the amplitude of displacement of the ciliary muscle. If the amplitude is insufficient, the accommodation will also be insufficient. In the ophthalmic assembly described here, contraction of the muscles could be used to recharge a battery. There is therefore no direct connection between the amplitude of movement of the muscles and the magnitude of the change in the focal length of the variable-focus lens. As a general rule, an ophthalmic assembly as described herein is implanted in a patient's eye which at least partially lost the accommodation functions. Therefore, the ciliary muscles are usually not used as an energy source.

It is possible to combine several sources of energy such as a photovoltaic cell and a rechargeable battery.

The source of energy is connected to the various components and/or units (autofocus system, signal processing unit, . . . ) so as to provide them with the energy necessary to perform their functions.

In the case where the power supply 16 is rechargeable, for example in the case of a battery or a supercapacitor, recharging means are to be provided. According to an advantageous embodiment, the ophthalmic assembly 10 comprises an antenna 29 disposed on the periphery of the support 17. This antenna 29 can be used to recharge the power supply 16 by electromagnetic induction.

Figure 9:
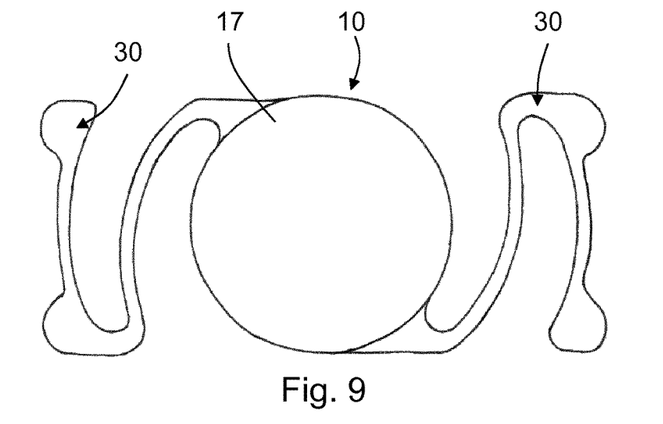
FIG. 9 illustrates a possible shape of the ophthalmic assembly of the invention.

The support 17 of the ophthalmic assembly 10 receives the different components described previously, namely the variable-focus lens 11, the actuator 12, the autofocus system 13, the signal processing unit 14, the actuator control unit 15, the power supply 16 and possibly communication means. This support 17 further comprises means 30 for maintaining the ophthalmic assembly 10 in place in the anterior chamber 31 of the eye of the patient. This maintaining means 30 can have different shapes such as haptic. Two of these shapes are illustrated by FIGS. 1 and 9.

Since the ophthalmic assembly is placed in the anterior chamber 31 of the patient's eye and since an intraocular lens 18 may be placed in the posterior chamber 19 of the same patient's eye, it is important that the shape of the support as well as the maintaining means 30 are compatible with the size and shape of the anterior chamber 31.

According to an aspect of the present invention, an ophthalmic assembly set is provided, comprising two ophthalmic assemblies as described above, one for each eye of a user. In embodiments of such ophthalmic assembly sets, each of the ophthalmic assemblies comprises a communication means for communicating between the two assemblies when they are each implanted in separate eyes of a user. This provides for bilateral operation where the functionality of one variable focus lens depends on the operation of the other and vice versa, which may help to provide autofocusing with a higher reliability for example, where communications between the two assemblies allow for each of them to confirm which object the user is most likely to be looking at.

The method for accommodating the vision of a patient functions as described below. First, the autofocus system 13 determines a distance parameter related to an object the patient's eye is looking at. This distance parameter depends on the type of autofocus system used and on the implementation chosen for the ophthalmic assembly 10. The distance parameter can be the actual distance between the patient and the object. This parameter can also be a range of distance between the patient and the object. For example, it is possible to define distance ranges such as "near vision" for a viewing distance of less than 50 cm, "intermediate vision" for a viewing distance between 50 cm and 1.50 m and "far vision" for a viewing distance beyond 1.50 m. In this case, the distance parameter is simply one of the determined ranges. It is clear that it is possible to define more than three ranges and that the distance values for these ranges may be different from the given examples.

In the case where the autofocus lens 27 is movable, the distance parameter may be the distance between the autofocus lens 27 and the corresponding autofocus sensor 26 for which the contrast of the image of the object that the patient is looking at, as formed by the autofocus lens, is maximal.

In the case where the autofocus lens 27 is a variable-focus lens, the distance parameter is the focal length of this autofocus lens for which the contrast of the image of the object that the patient is looking at, as formed by the lens of the autofocus lens, is maximal.

In general, the distance parameter is a value determined by the autofocus system 13 and the signal processing unit 14, which make it possible to define what the focal length of the variable-focus lens 11 should be so that the image of the object that the patient is looking at, as formed by the lens with variable focus, is clear.

Several images are captured while varying the focal length of the autofocus lens 27 and the images are then transmitted to the signal processing unit 14. The signal processing unit 14 determines for which image, the contrast is maximal and at which focal length of the autofocus lens 27 this image corresponds. The signal processing unit then converts the value of the focal length of the autofocus lens 27 into a value of the focal length of the variable-focus lens 11. The value of the focal length of the variable-focus lens is transmitted as a target-value to the control unit 15 of the actuator. The actuator 12 then acts in such a way that the focal length of the variable-focus lens 11 reaches this target value. It is clear that the way of controlling the actuator 12 depends on the implementation chosen.

The object that the patient is looking at or in other words, the object that is used to determine a distance parameter, may be an area of the user's field of view. According to a preferred embodiment, this area is located around the center of the user's field of view and its extent is sufficiently small so that the distance between the possible different views of the scene that the user is looking at is not too great.

As mentioned above, the ophthalmic assembly 10 is placed in the anterior chamber 31 of the patient's eye 20. This ophthalmic assembly 10 can be implanted in an eye in which the lens has been replaced by an intraocular lens or in an eye with the natural lens.

In a first embodiment, the ophthalmic assembly 10 is implanted without taking into account the actual vision of the patient. The function of this ophthalmic assembly is to allow accommodation of vision by the patient. In this embodiment, the default focal length of the ophthalmic assembly cannot be changed once this ophthalmic assembly has been placed in the patient's eye.

According to another variant, the default focal length may be modified after implantation of the ophthalmic assembly in the patient's eye. This can for example be done by injecting or removing fluid from the variable-focus lens.

This variant makes it possible to adjust the default focal length of the variable-focus lens, so as to take into account the actual vision of the patient. The default focal length corresponds usually to distant vision for the patient. It corresponds to the focal length of the variable-focus lens in the absence of stimulation by the actuator 12. Thus, if the actuator is no longer powered, the lens 11 with variable focal length takes a configuration such that the user has a good distant vision.

The default focal length can be preset before the implantation of the ophthalmic assembly 10 in the patient's eye and can be modified or adapted after implantation, at least in some embodiments. The presetting of this default focal length can be made via the same mechanism as that which is used to modify the focal length during the use of the ophthalmic assembly. In another embodiment, the presetting can be made via a first mechanism while the modification of the focal length for the instant accommodation is made via another mechanism. An example of a possible embodiment is to use a lens containing liquid 23 and a pump 25 for presetting the default focal length and an actuator 12 comprising compression elements 21 in the form of two annular electrodes to execute the accommodation function.

In a typical embodiment, the focal length of the variable-focus lens varies in a range of −1 to +4 diopters and preferably from −0.5 to +3.5 diopters or from 0 to +3 diopters.

In a preferred embodiment, the ophthalmic assembly comprises communication means 32 for receiving information and/or commands from outside, and optionally for transmitting data to the outside. This communication means 32 comprises in particular an antenna 33. The antenna 33 of the communication means 32 may be the same as the antenna 29 used with the power supply 16, in the context of charging the battery by induction or may be a separate antenna or a separate inductive loop.

After placing the ophthalmic assembly 10 in the eye of a patient, an ophthalmologist can determine what the default focal length of the variable-focus lens 11 should be. It can then act, for example by means of a dedicated application, on the setting of this default focal length. The setting instructions of this default focal length can be received by the antenna 33 of the communication means 32 and processed by the signal processing unit 14. This signal processing unit can then act on the actuator control unit 15 to set the default focal length.

The default focal length can be set just after the implantation of the ophthalmic assembly 10 in the patient's eye. It can also be adjusted for example after a few months or years, when the vision of the patient has changed.

Still as an example, the user may also have an application allowing him to activate or deactivate the autofocus system 13. In the case where this user performs a task that does not require a constant focus of the viewing distance, for example for reading or working in front of a computer screen, the user could choose to disable the autofocus system. Such deactivation can be done by sending a signal received by the antenna 33 of the communication means 32 and processed by the signal processing unit 14. The actuator control unit 15 can then set the focal length of the variable-focus lens 11 to a defined value, which may for example correspond to the focal length of the lens just before deactivation, to a value or a range of vision selected by the user or to the default focal value. The user can then reactivate the autofocus system 13 by sending a corresponding signal to the ophthalmic assembly 10. According to an embodiment, deactivating the autofocus system 13 can be done by suppressing the power supply of the actuator 12. Depending on the implementation, this can lead to the variable-focus lens 11 to remain in the state it reached just before the deactivation. In another implementation, this can also lead to the variable-focus lens taking the value of the default focal length.

The antenna 33 of the communication means 32 can also be used to send a signal to the outside. This could especially be done when the power supply 16 needs to be recharged. In this case, an alert signal can be sent by means of the antenna 33 to an appropriate reading device or interactive device, such as a smartphone. Such a reading device or interactive device could also be used to interrogate the ophthalmic assembly and for example to know the energy available, to receive an estimate of the remaining battery life, etc.

The ophthalmic assembly according to the invention can be implanted in a patient independently of the correction of the vision. It can for example restore the accommodation of the vision to a user who lost accommodation while keeping the natural lenses of the eyes. In this context, this ophthalmic assembly can be used for example by a spectacle wearer as an alternative to progressive spectacles. In this case, the basic correction of the vision is given by a pair of non-progressive spectacles. The accommodation function is provided by the ophthalmic assembly. This can be of particular interest for people who do not tolerate progressive glasses. This can also be of particular interest for people who wear contact lenses.

The ophthalmic assembly according to the invention also makes it possible to correct, to a certain extent, the vision of a patient following a lens replacement operation. Refractive error post-surgery can be due, for example in the case of intraocular lenses, to the difficulties to make very precise biometric measurements and in any case, to changes in the patient's vision.

As the ophthalmic assembly deals mainly with accommodation and not with correction, the amplitude of the movements in the lens is quite small. This implies that the size of the ophthalmic assembly can be maintained small and that the requested power can be low. This also contributes to the reduction in size of the ophthalmic assembly.

This size reduction enables placing the ophthalmic assembly in the anterior chamber of the eye, which leaves space of an intraocular lens in the posterior chamber of the eye.

Embodiments of the present invention may employ micro-lens fabrication techniques as described below for the production of any of the autofocus lens systems described herein. A typical micro-lens may have a planar surface and a convex surface to refract the light. According to the type of micro-lens, the convex surface may be spherical or aspherical. Various layers of optical materials may also be used to achieve the desired refraction properties of the micro-lenses.

Two known types of micro-lens are the gradient index micro-lens (GRIN) and the micro-Fresnel lens. Some GRIN micro-lenses have two flat parallel surfaces for the passage of light, with the focusing action being achieved thanks to a variation of the refractive index across the lens. In other GRIN micro-lenses, one or other or both surfaces of the lens may have a convex or concave shape, the focusing power thereby being achievable by virtue of the shape of the surface or surfaces of the lens. In still other GRIN micro-lenses, the focusing action may be achieved both by the variation in refractive index across the lens and by the shape of the surface or shapes of the surfaces of the lens.

Micro-Fresnel lenses may generally be very thin and consequently very lightweight. This type of lens features a set of concentric curved surfaces, which contribute to the focusing action of the light. They have grooves with stepped edges or multi-levels that may be said to approximate the shape of an ideal lens. They have advantages in that their fabrication and replication may be achieved using standard semiconductor processing techniques.

Several different techniques are known for the fabrication of GRIN micro-lenses. These include Neutron Radiation Irradation, Chemical Vapour Deposition, Partial Polymerisation, Ion Exchange, Ion Stuffing and Direct Laser Writing. All of these techniques are well known, and each technique may have its own effect on the resulting micro-lens. For example, in Ion Exchange, glass is immersed into a liquid melt with lithium ions. As a result of diffusion, sodium ions in the glass are partially exchanged with the lithium ions, with a larger amount of exchanges occurring at the edge.

Micro-Fresnel lenses may be manufactured using a standard micro-fabrication process including masks or moulds, photo-resists and selective UV exposure. A UV-curable polymer may be deposited on a glass substrate for example. A mould having the desired pattern for the micro-Fresnel lens, e.g. a series of concentric grooves having sloping edges, is applied, using pressure, to the substrate having the UV-curable polymer. The pressure causes excess polymer, not protected by the mould, to be expelled. The remaining polymer is exposed to a UV light source from below the glass, thereby curing the polymer which remains in the mould. When the mould is removed, there remains a cured polymer profile having the desired form of concentric grooves having sloping edges defined by the mould, thereby providing the micro-Fresnel lens.

According to an embodiment in which the autofocus system comprises an autofocus lens system comprising a deformable lens, such a lens may be made using an active deformable micro-optofluidic lens array. Optofluidic lenses are those which contain a fluid, such as the liquid containing lenses mentioned previously. Micro-optofluidic lenses exhibit the feature of being micro-lenses as described above. When placed in an array, they made be used in embodiments of autofocus lens systems of the present invention. An array of micro-lenses may be formed by injecting the liquid into the lens array in which each of the adjacent lenses are connected such that the fluid can run through all of the lenses. If the injection is provided through the micro-lens array only during the manufacturing of the system and not during their deployment, then an array of fixed focal length micro-lenses can be realised. Curvatures of the micro-optofluidic lens membrane are fixed, but it is also possible to re-fill or drain the liquid inside the system to adjust the focal lengths after the injection step and on a lens by lens basis, thereby providing a suitable array having lenses with different fixed focal lengths for use in an autofocus lens system of an embodiment of the present invention.

The invention claimed is:

1. An intraocular lens (IOL) for implantation into an anterior chamber of an eye of a user, the ophthalmic assembly comprising:
 a support upon which is disposed:
  a variable-focus lens having a variable dioptric power and comprising an anterior elastomeric, non-permeable, and deformable membrane and a posterior rigid, transparent, and stationary face;
  an autofocus system configured to receive light from a target object upon which the user's gaze falls and to determine a distance parameter for the target object, said autofocus system comprising:
   an autofocus lens system located on the support adjacent to the variable-focus lens; and at least one autofocus sensor configured to measure a contrast value of at least part of an image formed on at least a part of the autofocus sensor by light passing through the autofocus lens system, the autofocus lens system being configured to cause light passing through at least a part of the autofocus lens system from the target object upon which the user's gaze falls to form an image which causes a maximal contrast to be measured on a part of the autofocus sensor, the autofocus system being configured to use a parameter of the autofocus lens system when the maximal contrast is measured to determine the distance parameter and to communicate the distance parameter to a processor;

a processor configured to convert the distance parameter to a control value;

an actuator configured to cause the dioptric power of the variable-focus lens to vary according to the control value; and at least one power source to provide power to the components of the assembly; wherein:

the actuator comprises at least one moveable compression element disposed on a periphery of the variable-focus lens on the support, the actuator being configured to move the compression element to cause the shape of the membrane to deform, thereby varying the dioptric power of the variable-focus lens.

2. The intraocular lens according to claim 1, wherein the autofocus lens system comprises a plurality of micro-lenses, each micro-lens having a different fixed focal length, the autofocus sensor having a plurality of regions each corresponding to one of the micro-lenses, each for receiving an image of the target object from light having passed through its corresponding micro-lens, the autofocus system being configured to use the focal length of the micro-lens whose image has the maximum contrast as the distance parameter.

3. The intraocular lens according to claim 2, wherein the autofocus system is further configured to extrapolate an extrapolated focal length from two adjacent micro-lenses whose images have close to the maximum contrast and to use the extrapolated focal length as the distance parameter.

4. The intraocular lens according to claim 1, wherein the autofocus lens system comprises a plurality of micro-lenses, each micro-lens having a different fixed focal length, the autofocus system further comprising a plurality of autofocus sensors, each autofocus sensor configured to receive an image of the target object from light having passed through its corresponding micro-lens, the autofocus system being configured to use the focal length of the micro-lens whose image has the maximum contrast as the distance parameter.

* * * * *